United States Patent [19]

Ciencewicki

[11] 4,340,556
[45] Jul. 20, 1982

[54] PRODUCTION OF FIBROUS SLIVER HAVING PARTICULATE MATTER DISTRIBUTED THERETHROUGH

[75] Inventor: Evelyn Ciencewicki, South River, N.J.

[73] Assignee: Personal Products Company, Milltown, N.J.

[21] Appl. No.: 213,439

[22] Filed: Dec. 5, 1980

[51] Int. Cl.³ .................................................. D04H 1/04
[52] U.S. Cl. ........................................ 264/119; 19/296; 128/285; 128/296; 264/109; 264/113; 264/122
[58] Field of Search ............... 264/109, 113, 119, 122, 264/131, 280, 282, 287; 19/296; 128/285, 296; 156/62.2, 62.6; 428/227, 240, 296

[56] References Cited

U.S. PATENT DOCUMENTS

| | | | |
|---|---|---|---|
| 2,409,066 | 10/1946 | Powell et al. | 264/119 |
| 2,483,406 | 10/1949 | Francis, Jr. | 264/113 |
| 2,910,763 | 11/1959 | Lauterbach | 128/296 |
| 3,047,444 | 7/1962 | Harwood | 264/122 |
| 3,063,453 | 11/1962 | Brecht | 128/285 |
| 3,399,671 | 9/1968 | Satas | 128/296 |
| 4,053,674 | 10/1977 | Buck, Jr. et al. | 264/122 |
| 4,105,033 | 8/1978 | Chatterjee et al. | 428/326 |
| 4,186,165 | 1/1980 | Aberson et al. | 264/113 |
| 4,268,340 | 5/1981 | Fitzgerald et al. | 264/122 |

Primary Examiner—James B. Lowe
Attorney, Agent, or Firm—Jason Lipow

[57] ABSTRACT

A fibrous sliver having particulate matter substantially homogeneously distributed therethrough is provided. The sliver is formed by first forming a low weight web of fibrous material and depositing unto said low weight web particulate material. The web is then compacted to the desired weight per unit area.

9 Claims, 8 Drawing Figures

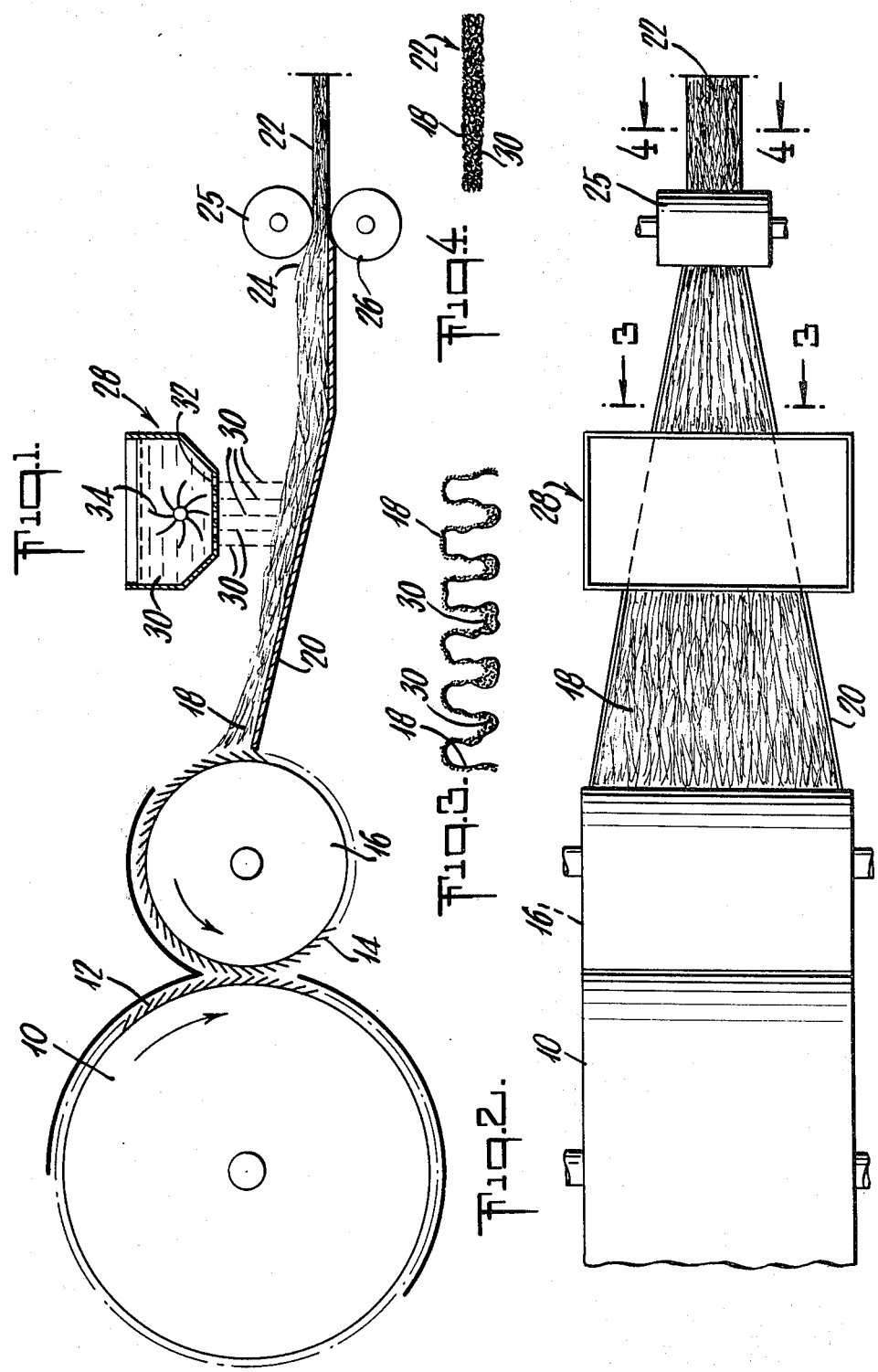

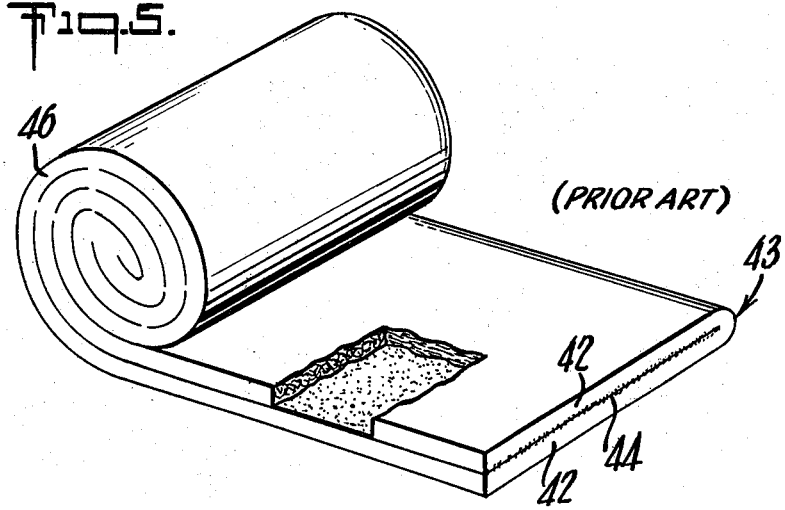
Fig. 5. (PRIOR ART)
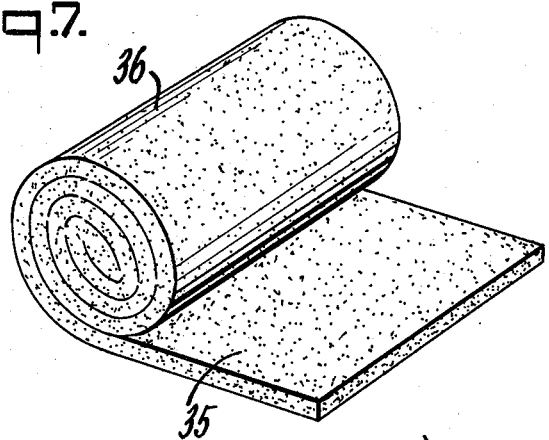
Fig. 7.
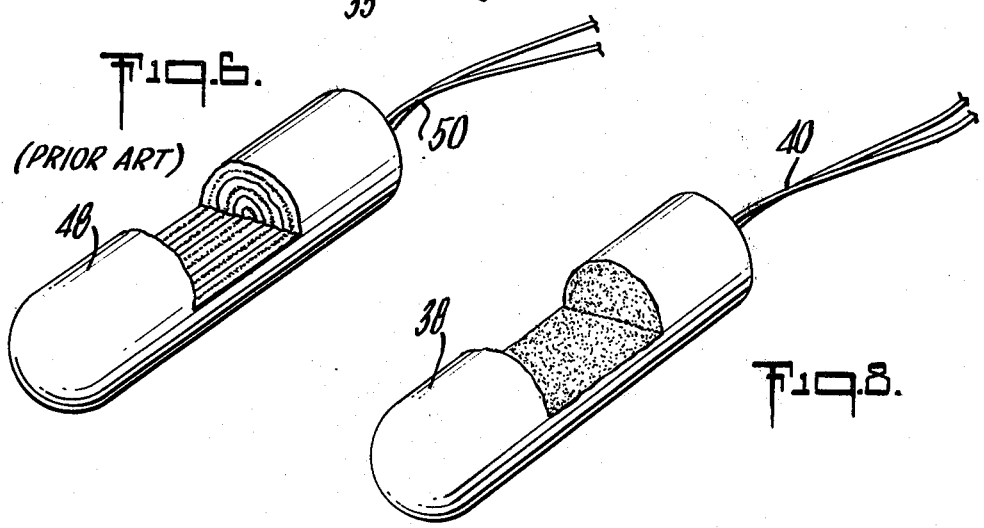
Fig. 6. (PRIOR ART)
Fig. 8.

PRODUCTION OF FIBROUS SLIVER HAVING PARTICULATE MATTER DISTRIBUTED THERETHROUGH

BACKGROUND OF THE INVENTION

This invention relates to fibrous slivers having particulate matter distributed therethrough and, particularly, to absorbent bodies made from such slivers and used in such body fluid absorbent products such as catamenial tampons and napkins, diapers, surgical sponges, wound dressings, and the like.

Products of this type are generally made from carded slivers of such fibrous material as cellulosic fibers; e.g., cotton or regenerated cellulosic fibers i.e., rayon, either in their natural chemical state, or more recently, in a chemically modified state which renders the fibers more absorbent. There are currently, on the market, body fluid absorbent products which contain, in addition to cellulosic fibrous absorbents, certain hydrophillic particulate materials which have been variously termed "super absorbents" or "hydrocolloids" and share the common characteristics of being highly absorbent and swellable and, hence, will greatly increase the absorbent capacity of these body fluid absorbing products. Additionally, it is sometimes desirable to include other particulate matter into absorbent bodies, such as, for example, deodorants and anti-microbial agents.

In general, these added particulate materials best perform their desired functions when they are dispersed as homogeneously as is possible within the absorbent body. When this is accomplished, the absorbent body will exhibit uniform physical properties and the likelihood for the particulate matter to dust out during the manufacturing and packaging process, during handling when storing or shipping, or in use will be minimized.

Unfortunately, it has heretofore been difficult to produce absorbent bodies comprising a sliver of fibrous absorbent material having, homogeneously distributed therethrough, particulate matter, in a manner commensurate with high speed manufacturing processes. This problem is acknowledged in U.S. Pat. No. 4,105,033 wherein the use of grafted cellulose powder in such products as catamenial tampons is described.

As is suggested in this patent, a simple method of distributing such powder is to merely sprinkle the powder onto the surface of a rectangular sliver of fibers and then to fold or roll the sliver into the desired shape of the absorbent body. While this solution no doubt offers the advantage of processing simplicity, the resulting product is far from the ideal of homogenous distribution and, instead, produces a product having alternating strata of fibrous web and particulate matter. The drawback of this construction is manifested in tampons, for example, by decreased absorbent capacity, increased "sloughing", i.e., the release of particulate matter from the tampon during handling and use, and increased "telescoping" i.e., the unraveling of the finished tampon after use.

Accordingly, there is a need for producing a sliver of relatively long fibrous material and relatively small particulate matter wherein the particulate matter is well distributed throughout the fibrous sliver.

SUMMARY OF THE INVENTION

It has now been discovered that a fibrous sliver can be manufactured having particulate material distributed therethrough wherein the particulate material is essentially homogeneously distributed. In particular, such a sliver may be produced by a process totally commensurate with high speed production.

As used herein the terms "fibrous sliver", "fibrous web" "web of fibrous material" are all used to denote material made up of relatively long fibers and are to be contrasted to the terms "particulate matter" or "particulate materials" which is used to denote material, in the form of fibers, flakes or powders, the largest dimension of which is relatively small. The relative sizes referred to above are in the ratio of at least about 1.5 to 1 and generally more than 2 to 1.

In accordance with this invention, the sliver is produced by first forming a web of fibrous material having a weight per unit area of from about 0.015 to about 0.100 times that desired in the finished sliver. The particulate matter is then deposited on the web and the web is then compacted to the finished sliver weight per unit area by reducing the width of the web by said factor of from about 10.0 to about 66.7. Preferably, the web is calendered after obtaining the reduced width and increased weight per unit area. The resulting product has an almost completely homogenous distribution of particulate matter and fibers. The method of this invention is best suited to slivers formed by carding machines wherein the compacted web is taken from the doffer of the carding machine and is increased in weight per unit area by decreasing its width until it obtains a weight per unit area of about 0.015 to about 0.10 times that desired for the finished sliver. At this point, particulate material is sprinkled or otherwise deposited onto the surface of the web and the web is then reduced further in width until the desired weight per unit area for the finished sliver is obtained. The sliver is then calendered to produce the finished sliver.

In a specific embodiment, the web is formed having a weight per unit area of from about 3.85 to about 13.42 gm/yd$^2$. About 0.05 to about 0.5 gm. of particulate matter per gram of web is sprinkled onto the surface of the web. The web is then compacted by reducing its width by a factor of from about 10.0 to about 66.7 to produce a sliver having a weight per unit area of about 153.9 to about 255.1 gm/yd. The thickness and density of the sliver is controlled by calendering the sliver.

It should be noted that, as used herein, the term "weight per unit area" is meant to denote the gross weight of the fabric residing over a surface area measured by a one inch length of fabric and bounded by the width of the fabric, said weight being divided by such area. Further, such weight is exclusive of any added particulate materials.

BRIEF DESCRIPTION OF THE DRAWINGS

FIG. 1 is a schematic side elevational view of a production line for producing the sliver of this invention;

FIG. 2 is a schematic plan view of the production line illustrated in FIG. 1;

FIG. 3 is a cross-sectional view of the intermediate web which ultimately is formed into the sliver of this invention, taken along line 3—3;

FIG. 4 is a cross-sectional view of the finished sliver, taken along line 4—4;

FIG. 5 is a perspective view of a partially rolled blank for a catamenial tampon as is shown in the prior art with parts removed to illustrate its construction;

FIG. 6 is a perspective view of a finished prior art tampon made from the blank of FIG. 5, with parts removed to illustrate construction;

FIG. 7 is a perspective view of a partially rolled blank for a catamenial tampon made from a sliver of this invention; and FIG. 8 is a perspective view of a finished tampon made from the blank of FIG. 7.

DETAILED DESCRIPTION OF THE INVENTION

Illustrated in FIG. 1, in schematic side elevational view, is a production line for making a sliver embodying the teachings of this invention. Fibers are carried on the partially illustrated cylinder 10 of a carding machine by the teeth 12 of the card clothing of the cylinder 10. Such fibers have been fed into the carding machine, generally in the form of lap rolls and may comprise for example such commonly used cellulosic fibers such as cotton or the like, regenerated cellulosic fibers; i.e., rayon staple, chemically modified cellulosic fibers, such as ethers and esters of cellulosic exemplified by carboxymethoxy cellulose or grafted interpolymers of cellulose such as those described in U.S. Pat. No. 3,889,678 issued to Proney Chatterjee, et al. on June 17, 1975. In the embodiment of this invention in which slivers are prepared for use in catamenial tampon production, the fibers fed to the carding machine are preferably a blend of cotton combers and staple rayon. The cotton combers have an arithmetic average fiber length of about 5 to 12 mm. The rayon fibers have a staple length of from one to two inches. While the proportions of rayon to cotton may vary widely, a highly satisfactory product is obtained when the percentage of cotton, based on the weight of the rayon-cotton mixture, varies from about 10 to about 50%.

The purpose of the carding process, as is well known in the art, is variously, to reduce the weight per unit area of the feed material, clean the feed material, disentangle the fibers and separate the bunches, tufts, or knots into individual fibers and generally orient the fibers in the machine direction. These objectives are accomplished, in alternative forms of carding machines, by transferring the fibers from teeth on the surface of sequentially aligned cylinders while applying various devices to comb and brush the fibers and while providing means for screening out undesirable fractions of the feed material. A suitable carding machine is revolving flat card manufactured by the Saco-Lowell Company of Waltham, Mass. U.S.A.

The combed and carded fibers are transferred from the teeth of the cylinder clothing 12 to the finer teeth 14 of the clothing of the doffer 16 which rotates in a direction counter to that of the cylinder. Various means, known in the art, may be employed for striping the now fully carded and combed fibers from the doffer. One such system accomplishes this task by use of vacuum stripping and is generally known the art as a Saco-Lowell vacuum stripper.

Irrespective of how this stripping is accomplished, the fibers are removed from the doffer in the form of a gossamer-like web 18, generally oriented in the machine direction, and fed onto the surface of a width-reducing pan 20. As the web 18 leaves the doffer, its weight per unit area is extremely low as compared with that of the finished sliver 22 and may be, for example, as little as 0.01 times the weight per unit area of the finished sliver 22. Preferably, however, the formed web is about 0.025 to about 0.075 times the finished weight per unit area. In terms of absolute values, for example, the finished sliver for use in catamenial tampons, may have a weight per unit area of about 200 gm/yd$^2$, in which case the web formed immediately upon stripping from the doffer would have a weight per unit area of from about 5 to about 15 gm/yd$^2$; i.e., about 10 gm/yd$^2$. I, for example, the desired width of the finished sliver is about two inches, and the web width from the doffer is about three feet, then a throughput through the carding machine of about 11 gm/linear yard will produce the desired weights per unit area.

The web formed from the doffer is compacted by pulling it through the width reducing pan 20 which may be a trough-like surface of gradually diminished width. As the web is so moved through the reducing pan, it is gathered into a series of pleats extending longitudinally in the machine direction and distributed across its width, and concommitantly, the weight per unit area is increased until the web is compacted to the desired weight per unit area of the finished sliver. The thickness and density of the finished sliver is controlled by having the web pass through the nip 24 of two cooperating calender rollers 25, 26 which is essence compress the web by collapsing the gathered pleats.

In accordance with the teachings of this invention, particulate matter is introduced into the finished sliver by depositing such matter onto the web at a point wherein the web has not yet been compacted into the final weight per unit area but instead is substantially less compacted; e.g., at a point intermediate to the doffer and the calender rollers while the web is in the width reducing pan. The precise point at which such material is best deposited will vary depending upon the nature of the particulate material being deposited and in particular upon the size of the particulate material.

Exemplary particulate material deposited onto webs ultimately to be used in body absorbent products may be the so-called hydrocolloids which consist of particles; i.e., powders, fibers, or the like, of water insoluble but highly water swellable polymeric substances capable of absorbing water in an amount that is at least ten times their own dry weight and is preferably about 15 to about 70 times the dry weight or more.

Such material may be described chemically as having a backbone of natural or synthetic polymers with hydrophilic groups, or polymers containing hydrophilic groups, chemically bonded thereto or in intimate admixture therewith. Included in this class of material are such modified natural and regenerated polymers such as polysaccharides including, for example, cellulose and starch and regenerated cellulose, which are modified by being carboxyalkylated, phosphonoalkylated, sulphoalkylated, or phosphorylated to render them highly hydrophilic. Such modified polymers may also be crosslinked to enhance their hydrophilicity and render them water insoluble.

These same polysaccharides may also serve, for example, as the backbone onto which other polymer moieties may be bonded by graft copolymerization techniques. Such grafted polysaccharides and their method of manufacture are described in U.S. Pat. No. 4,105,033 issued on Aug. 8, 1978, to P. K. Chatterjee, et al. and may be described as polysaccharide chains having grafted thereon a hydrophilic chain of the general formula:

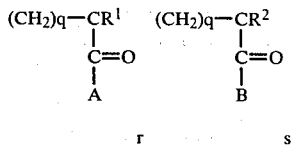

wherein A and B are selected from the group consisting of —OR$^3$, —O(alkalki metal), —ONH$_4$, —NH$_2$, wherein R$^1$, R$^2$ and R$^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1 and q is an integer having a value of 1 to 4.

The preferred hydrophilic chains are hydrolyzed polyacrylonitrile chains and copolymers of polyacrylamide and sodium polyacrylate.

In addition to modified natural and regenerated polymers, the hydrocolloid particles may comprise wholly synthetic hydrophilic particles. Examples of those now known in the art are polyacrylonitrile fibers which may be modified by grafting such moieties thereon such as polyvinyl alcohol chains, polyvinyl alcohol itself, hydrophilic polyurethane, poly(alkyl phosphonates) partially hydrolyzed poly acrylamides (e.g., poly (N-N-Dimethyl acrylamide), sulfonated polystyrene, or poly (alkylene oxide). These highly hydrophilic synthetic polymers may be modified by other chemical treatments such as cross-linking or hydrolysis.

The hydrocolloid particles may take various physical shapes such as powders, fibers or flakes. Specific examples are fibers of carboxyalkylated cellulose, powders of carboxyalkylated starch or ground fibers of the grafted polysaccharides described in the aforementioned U.S. Pat. No. 4,105,033.

Preferably, for use in catamenial tampons, the particulate matter is a hydrocolloid having an average particle size range of from 0.03 to 3.0 mm and desirably in the shape of fibers. In this particle size range, it is desirable to deposit this particulate matter onto the web when the web has a weight per unit area of from about 0.015 to about 0.1 times that of the finished sliver. For example, in terms of absolute numbers, for a sliver having a weight of from 3.85 to 13.42 gm/yd$^2$, the particulate material should be deposited on the web at a point wherein the web has a weight of 5.2 to about 72.9 gm/yd$^2$. It has been discovered that by so positioning the point of deposition, the web has sufficient compaction to retain the bulk of the particulate matter. At the same time, the web is capable of being further compacted so as to get the desired homogeneous distribution of particulate matter throughout the finished sliver.

Any suitable means for depositing the particulate material onto the surface of the web at the prescribed position may be employed. One such means, illustrated in FIGS. 1 and 2, is to provide a hopper or other similar supply container 28 of particulate matter 30. The hopper 28 is provided with a perforated bottom e.g., a screen 32, having apertures of sufficient size to permit the controlled release of the particulate matter onto the web. A rotating rake 34 or similar means may be employed to further control the flow of particular material from the hopper, through the screen and onto the web. It will be understood by those skilled in the art that other means for depositing the material onto the web may be employed, including, for example, reciprocating shakers and vibrating screen devices.

FIG. 3 is a cross-sectional view of the web taken along line 3—3 of FIG. 2; i.e., just downstream of the deposition point. As is illustrated therein, the fibrous web 18 is loosely gathered into longitudinally extending pleats distributed across the width of the web. The particulate matter 30 tends to settle and fill in the troughs of those pleats thus forming, in transverse cross-section, an alternating series of columns of fiberous web and particulate matter. The illustrated width reducing pan has a generally flat surface and the pleating of the web 18 is a manifestation of pulling the web through the pan of continuously reduced width. Should it be desirable to more closely control the size and frequency of the pleats, it will be understood that such control can be accomplished by varying the surface of the pan; e.g., provide a series of longitudinally extending ribs upstanding from the surface of the pan.

The pleated web, bearing the deposited particulate matter, proceeds toward the nip 24 of the calender rollers 25 and 26 and becomes more and more compacted owing to the reduced width of the pan. At the calender rollers, the web now has the weight per unit area desired in the finished sliver. The nip 24 of the rollers 25, 26 is adjusted to provide the degree of compression needed to compress the sliver to its desired height and density. Generally, slivers suitable for use in catamenial tampons will have a thickness or height of about 5.00 to 10.0 mm and a density of about 0.2 to 1.2 gm/cc. FIG. 4 illustrates the finished sliver 22 in cross-sectional view, taken along line 4—4 of FIG. 2. As illustrated, the pleats have been compacted by the pan and collapsed by the calender rollers producing, in essence, a sliver having homogeneously distributed particulate matter 30 therethrough.

EXAMPLE 1

A sliver is prepared in accordance with the process described in connection with FIG. 1. The feed material is a lap of staple rayon and cotton comber fibers wherein the rayon fibers have a staple length of 1½–1 9/16 inches and the cotton comber fibers are about 9 mm in length. The lap comprises approximately 75%, by weight, rayon fibers, the remainder being the cotton comber fibers. The feed lap is fed through a Saco-Lowell Card at the throughput rate of approximately 11.25 gm. per linear yard. A gossamer-like web of carded fibers is stripped from the doffer and pulled through a width reducing pan and through the nip of calender rollers. The width reducing pan has an upstream width of 38 inches and reduces to 2 inches within a length of 30 inches. The web leaving the doffer has a weight of 10.6 gm/yd$^2$ and the finished 2-inch wide sliver has a weight of 203.4 gm/yd$^2$. At the point where the width reducing pan is approximately 18 inches wide and the web has a weight of about 22.5 gm/yd$^2$, a hopper of the type shown in connection with FIG. 1 straddles the reducing pan and deposits onto the web a hydrocolloid particulate material. The particular material employed is that described in U.S. Pat. No. 3,889,678 and, specifically, sample number 4, in Table II, of that patent. This material is a cellulose graft copolymer consisting of a cellulose backbone having grafted thereto polymer moities consisting of copolymers of sodium acrylate and ethylacrylate in a weight ratio of 19.8 parts by weight cellulose to 33.9 parts by weight of poly(ethylacrylate) to 46.3 parts by weight of poly (sodium acrylate). This hydrocolloid is in fibrous form with the fibers having an arithmetic average fiber length of approximately 0.8 mm. Approximately 15 gms of hydrocolloid material is deposited per 85 gm of rayon-cotton web. The sliver is pulled through the nip of the rollers which is set at a gap of less than ¼ inch providing a sliver having a density of about 0.029 gm/cc. The resulting product is one in which the sliver has the particulate hydrocolloid well distributed therethrough.

EXAMPLE 2

A series of catamenial tampons are made from the sliver described in connection with Example I above. Referring to FIG. 7, the long sliver comprising a relatively homogeneous mixture of fibers 18 and particles 30, is divided into rectangular pads measuring 9 inches in length (the carding machine direction) and 2 inches in width. A cylindrical tampon blank 36 is formed by rolling a pad 35 from one end to the other in a direction parallel to the longitudinal sides of the pad. The rolled pad is then compressed in a die to the desired tampon shape 38, as is illustrated in FIG. 8. The tampon is provided with the usual withdrawal string 40 which may be sewn through the removal end of the tampon. For this example, the string is applied by looping the same around the rectangular pad prior to rolling the pad into a blank. For simplicity, this is not shown in FIG. 7.

A second series of tampons are prepared for comparative purposes. Rectangular pads measuring 9 inches by 2 inches wide are prepared from slivers made essentially in the same manner as described above with the exception that such slivers are, of course, wider and no particulate material is deposited thereon. Particulate matter of the type described above is then added to this pad in the manner described in the aforementioned U.S. Pat. No. 4,105,033, i.e., by sprinkling such particulate matter onto the surface of the pad. The pad is then folded along a longitudinal center line 43, as is illustrated in FIG. 3, to form a double layer of fibrous webs 42 sandwiching therebetween a layer of particulate matter 44. The pad is then rolled into a cylindrical tampon blank 46 as illustrated and in the manner described in connection with FIG. 7.

The blank 46 is compressed in a die into the final tampon shape 48, as is illustrated in FIG. 6, with a withdrawal string 50 being provided as is described above.

The two series of tampons are each tested, non-menstrually, by panels of women to determine the respective resistances to sloughing; i.e., the breaking and dusting of particles from the surface of the tampon. The women are instructed to use the tampons for two hours. Thereafter, the tampons are returned and evaluated by a judge who assigns a numeric value to the degree of fiber disturbance observed by comparing each tampon to ranked pictorial standards. The numeric ranking system is as follows:

| Sloughing Score | Degree of Fiber Disturbance |
| --- | --- |
| 0 | none |
| 2 | slight |
| 4 | moderate |
| 8 | excessive |

The results of the test are recorded below:

| Sample | No. of Panelists | Average Sloughing Score |
| --- | --- | --- |
| Prior Art Tampons | 10 | 3.0 |
| Homogenous Tampons | 20 | 1.6 |

As is evident from the above table, a substantial degree of sloughing resulted when the prior art tampons of the type illustrated in FIGS. 5 and 6 were employed. In contrast therewith, use of the homogeneous tampons of this invention, as illustrated in FIGS. 7 and 8, resulted in a great decrease in sloughing.

What is claimed is:

1. A method for producing a fibrous sliver having particulate material distributed therethrough wherein the largest dimension of said fibrous material is at least 1.5 times that of the particulate material, said method comprising:
   first forming a gossamer-like web;
   compacting said gossamer-like web to form a low weight web of fibrous material having a weight per unit area of from about 0.015 to about 0.10 times that desired in the finished sliver;
   depositing said particulate material only onto said low weight web; and
   compacting the web by reducing its width by a factor of about 10.0 to about 66.7 to form the sliver.

2. The method of claim 1 wherein the largest dimension of said fibrous material is at least 2.0 times that of the particulate material.

3. The method of claim 1 wherein said gossamer-like web is formed into a low weight web having longitudinal pleats and a substantial portion of said particulate material is deposited in the trough of said pleats.

4. The method of claim 1 wherein said sliver is calendered after being formed by compacting.

5. The method of claim 4 wherein said sliver is calendered to a density of about 0.2 to about 1.2 gm/cc.

6. The method of claim 1 wherein said low weight web has a weight per unit area of from about 3.85 to about 13.42 gm/yd$^2$.

7. The method of claim 1 wherein said sliver has a weight per unit area of about 154 to about 255 l gm/yd$^2$.

8. The method of claim 1 wherein about 0.05 to about 0.5 grams of particulate matter per gram of low weight web is deposited on said low weight web.

9. The method of claim 1 wherein said particulate matter is sprinkled onto the surface of said low weight web.

* * * * *

UNITED STATES PATENT AND TRADEMARK OFFICE
CERTIFICATE OF CORRECTION

PATENT NO. : 4,340,556
DATED : July 20, 1982
INVENTOR(S) : Evelyn Ciencewicki

It is certified that error appears in the above—identified patent and that said Letters Patent are hereby corrected as shown below:

Column 8, Line 52, "255 I gm/yd$^2$." should be --255 gm/yd$^2$.--

*Signed and Sealed this*

*Twenty-sixth* Day of *October 1982*

[SEAL]

*Attest:*

*Attesting Officer*

GERALD J. MOSSINGHOFF
*Commissioner of Patents and Trademarks*